US012702730B2

(12) United States Patent
Adesida et al.

(10) Patent No.: US 12,702,730 B2
(45) Date of Patent: Aug. 11, 2026

(54) ENGINEERED CARTILAGE

(71) Applicant: STEMCELLAGO INC., Edmonton (CA)

(72) Inventors: Adetola Bamidele Adesida, Edmonton (CA); Martin Osswald, Edmonton (CA); Khalid Ansari, Edmonton (CA); Hadi Seikaly, Edmonton (CA)

(73) Assignee: STEMCELLAGO INC., Edmonton (CA)

( * ) Notice: Subject to any disclaimer, the term of this patent is extended or adjusted under 35 U.S.C. 154(b) by 911 days.

(21) Appl. No.: 17/660,876

(22) Filed: Apr. 27, 2022

(65) Prior Publication Data

US 2022/0347349 A1 Nov. 3, 2022

Related U.S. Application Data

(60) Provisional application No. 63/197,678, filed on Jun. 7, 2021, provisional application No. 63/182,190, filed on Apr. 30, 2021.

(51) Int. Cl.

| | |
|---|---|
| ***A61L 27/38*** | (2006.01) |
| ***A61L 27/36*** | (2006.01) |
| ***C12N 5/077*** | (2010.01) |
| ***C12Q 1/6881*** | (2018.01) |

(52) U.S. Cl.

CPC ....... *A61L 27/3852* (2013.01); *A61L 27/3612* (2013.01); *A61L 27/3654* (2013.01); *A61L 27/3817* (2013.01); *A61L 27/3895* (2013.01); *C12N 5/0655* (2013.01); *C12Q 1/6881* (2013.01); *C12N 2501/115* (2013.01); *C12N 2501/15* (2013.01); *C12N 2502/1358* (2013.01); *C12N 2513/00* (2013.01)

(58) Field of Classification Search

CPC ............. A61L 27/3817; A61L 27/3852; A61L 27/3612; A61L 27/3654; A61L 27/3895; C12N 5/0655; C12N 2501/115; C12N 2501/15; C12N 2502/1358; C12N 2513/00; C12Q 1/6881

See application file for complete search history.

(56) References Cited

U.S. PATENT DOCUMENTS

| | | | | |
|---|---|---|---|---|
| 10,100,274 B2 * | 10/2018 | Taniguchi | ............... | A61P 43/00 |
| 2016/0334392 A1 * | 11/2016 | Gothelf | ................... | A61P 37/00 |
| 2020/0147269 A1 * | 5/2020 | Roël | ...................... | G01N 33/68 |
| 2022/0390466 A1 * | 12/2022 | Toler | ...................... | G16H 50/20 |

FOREIGN PATENT DOCUMENTS

| | | | | |
|---|---|---|---|---|
| AU | 2015207888 A1 * | 2/2017 | ............... | A61N 2/02 |
| CN | 112370573 A * | 2/2021 | ......... | A61L 27/3817 |
| EP | 2669384 A1 * | 12/2013 | ........... | C12Q 1/6883 |
| WO | WO-2017156591 A1 * | 9/2017 | | |
| WO | WO-2019101956 A1 * | 5/2019 | ........... | A61K 31/167 |
| WO | WO-2020150552 A2 * | 7/2020 | ......... | A61K 31/4155 |

OTHER PUBLICATIONS

Mume et al. (Lancet(2016) vol. 388 p. 1985-1994) (Year: 2016).*

Diniz de Pochat et al (Aesthetic Surgery Journal(2011) 31(8) 891-896) (Year: 2011).*

Hamada et al. (Nagoya J. Med. Sci.(2013) 75:101-111) (Year: 2013).*

Cheng Machine Translation CN 112370573 A (Year: 2017).*

O'Sullivan et al (Stem Cell Research and Therapy(2011)2:8;1-7) (Year: 2011).*

Seol et al (Arhritis Rheum (2012)64(11)1-20) (Year: 2012).*

Wu et al (Stem Cell Reports(2013)1;575-589) (Year: 2013).*

Sanchez et al (Osteoarthritis and Cartilage (2017)1199-1209) (Year: 2017).*

Cheng et al (Stem Cells and Translational Medicine (2019) 9;1-13, referred to as ChengA) The influence of fibroblast growth factor 2 on the senescence of human adipose-derived mesenchymal stem cells during long-term culture (Year: 2019).*

Lotz et al (JCI (1992) 90:3;1-10) Leukemia Inhibitory Factor Is Expressed in Cartilage and Synovium and Can Contribute to the Pathogenesis of Arthritis (Year: 1992).*

Beederman et al (J Biomed Sci Eng (2013) 6:8A;1-33) Bmp signaling in mesenchymal stem cell differentiation and bone formation ( Year: 2013).*

Hsieh et al (Stem Cells and Devlopment (2010) 19:12;1-16) Functional Module Analysis Reveals Differential Osteogenic and Stemness Potentials in Human Mesenchymal Stem Cells from Bone Marrow and Wharton's Jelly of Umbilical Cord (Year: 2010).*

Hector Martinez Avila et al : "3D bioprinting of human chondrocyte-laden nanocellulose hydrogels for patient-specific auricular cartilage regeneration", Bioprinting, vol. 1-2, Mar. 1, 2016 (Mar. 1, 2016), pp. 22-35.

Lim Mi Hyun et al: "Evaluation of Collagen Gel-Associated Human Nasal Septum-Derived Chondrocytes as a Clinically Applicable Injectable Therapeutic Agent for Cartilage Repair", Tissue Engineering and Regenerative Medicine, Springer Singapore, Singapore, vol. 17, No. 3, May 12, 2020 (May 12, 2020), pp. 387-399.

(Continued)

*Primary Examiner* — James D Schultz
*Assistant Examiner* — Andrea Lynne Morris Spencer
(74) *Attorney, Agent, or Firm* — NORTON ROSE FULBRIGHT CANADA LLP

(57) ABSTRACT

It is provided a method of producing high-quality engineered cartilage graft in a human of animal, such as nasal cartilage graft, comprising expanding chondrocytes and/or chondroprogenitors, e.g. autologous human nasoseptal chondrocytes (hNC,) from a donor patient by selecting expanded chondrocytes and/or chondroprogenitors by detecting the expression of at least one surfaceome protein gene or secretome protein gene, wherein the at least one surfaceome protein gene is ADGRG1, NPR3, SLC16A4, TSPAN13, FZD4 and SLC22A23 and the at least one secretome protein gene is ADGRG1, B3GNT7, COLGALT2, IGFBP3, STC2, SAA1, ANGPLT1, COL8A2, INHBB, ADAMTS9, ORM1, COL14A1, DCN, COL21A1, ENOX1, IL7, MXRA5 GAL, TFRC, SERPINA9, LIF, GDF6 and COL5A3.

14 Claims, 9 Drawing Sheets

(56) References Cited

OTHER PUBLICATIONS

Anderson-Baron Matthew et al: "Suppression of Hypertrophy During in vitro Chondrogenesis of Cocultures of Human Mesenchymal Stem Cells and Nasal Chondrocytes Correlates With Lack of in vivo Calcification and Vascular Invasion", Frontiers in Bioengineering and Biotechnology, vol. 8, Jan. 5, 2021 (Jan. 5, 2021), pp. 1-16.

Stull Robert A et al: "Expression analysis of secreted and cell surface genes of five transformed human cell ines and derivative xenograft tumors", BMC Genomics, Biomed Central Ltd, London, UK, vol. 6, No. 1, Apr. 18, 2005 (Apr. 18, 2005), p. 55.

Grogan, S.P. et al. "Identification of Markers to Characterize and Sort Human Articular Chondrocytes with Enhanced in Vitro Chondrogenic Capacity". Arthritis & Rheumatism, vol. 56, No. 2, 2007, pp. 586-595.

Fulco, I. et al., "Engineered autologous cartilage tissue for nasal reconstruction after tumour resection: an observational first-in-human trial". Lancet, vol. 384, 2014, pp. 337-346.

Szojka, A.R.A. et al. "Human engineered meniscus transcriptome after short-term combined hypoxia and dynamic compression". Journal of Tissue Engineering, vol. 12, 2021 pp. 1-15.

* cited by examiner

Fig. 12

ENGINEERED CARTILAGE

CROSS-REFERENCE TO RELATED APPLICATIONS

The present application claims benefit of U.S. Provisional Application Nos. 63/182,190 filed Apr. 30, 2022 and 63/197,678 filed Jun. 7, 2021, the content of which are herewith incorporated in their entirety.

TECHNICAL FIELD

It is provided a method of selecting and producing high-quality engineered cartilage graft.

BACKGROUND

More than 3 million people were treated for skin cancers in 2015 in North America. Non-melanoma skin cancer (NMSC) is the most common cancer diagnosed in Canadians. Most cancer registries in Canada do not collect information about NMSC as they are difficult to keep track of. The information often goes unreported because NMSC is usually diagnosed and treated easily in the doctor's office. For this reason, the actual numbers of NMSC cases are difficult to know. Taking the Alberta province as a test case, the most recent review states that between 1998 and 2007, a total of 98,645 people were diagnosed with NMSC. In one Alberta clinic, 5-6 patients per week are seen with cancer on their noses. Most NMSC arise in body areas exposed to the sun, with the highest frequency (36%) of location on the nasal lobule.

The standard treatment is total local excision of the cancer. However, tumor resection could lead to defect in the subcutaneous tissue, underlying fatty tissue and loss of more than 50% of the nasal alar lobule cartilage. In these cases, the invasiveness of the resection affects structural integrity of the lobule and its function. Moreover, the changes in the aesthetical appearance can be distressful to the patients. The structural framework of the nose is made of cartilage. The greater alar cartilages are paired wing-shaped structures, that form the outer eminence of the nostril. These structures, also known as the lower lateral cartilages (LLC), provide the dual function of conferring the intricate nuances of the aesthetic shape of the nasal tip and the nostrils while providing critical support to the nasal vestibular airway. The nasoseptal cartilage is the structural cartilage in the center of the nose and it is primarily responsible for setting the projection of the external nose. When these cartilages are sacrificed during the treatment of a nasal tip skin cancer with surgery, it can be extremely challenging to recreate this complex cartilaginous structure with existing reconstructive techniques.

Currently, reconstruction of the LLCs or nasal septum requires the harvest of cartilage grafts from either the concha of the ear or the costal cartilage of the ribs. The procedures themselves can impart significant donor site morbidity for the patient such as surgical site pain, infection, scarring, deformity, and even life-threatening complications such as pneumothorax when harvesting rib cartilage. Once the cartilage graft has been harvested from the secondary site, it must be carved to the appropriate shape by the surgeon, which can be extremely time consuming and technically challenging, increasing the cost of the overall reconstruction. Despite meticulous carving, such in situ grafts may still undergo warping, and shifting in position due to scar contracture, leading to poor aesthetic and functional results for the nose.

Bioprinting of engineered cartilages is a promising strategy to replace the need for harvesting and carving in situ cartilage grafts and eliminating secondary donor morbidity for the patient. Nasal cartilage composition is similar to that of joint (articular) cartilage, with ~80% water, and remainder predominantly composed of collagens (7.7%), sulfated glycosaminoglycans (GAG, 3%) and cells (~$25\times10^6$ cells/g of tissue). Previous work has demonstrated co-expression of both types I and II collagen throughout the human nasal septum. Structurally, the nasal septum acts as a support strut, much like a tent post to maintain an open external nasal airway. This mechanical role would result in the nasal septum undergoing predominantly bending stresses from the overlying skin's pressures and attached muscles. The distribution of types I and II collagen combined with the GAG results in a compliant structure that can move under normal loading without failing and maintaining the nose's external projection.

Human nasoseptal chondrocytes (hNC) has been a target cell source for engineering both nasal cartilage and articular cartilage in the knee. hNC is easily isolated from a biopsy of the nasoseptal cartilage. hNC is expanded in vitro culture with fibroblast growth factor 2 (FGF-2) and transforming growth factor beta-1 (TGFβ1) or T1F2 (combination of FGF-2 and TGFβ1) for short to enhance hNC's capacity to re-express the functional extracellular matrix (ECM) of nasal cartilage after cell expansion. hNC has been shown to produce functional ECM after more than 10 population doublings in monolayer expansion culture. This indicates that a small biopsy of nasoseptal cartilage can be used to obtain sufficient hNC for the fabrication of large functional grafts. hNC has been used to engineer autologous cartilage grafts in a first clinical trial, involving 5 patients with NMSC on the nose. The grafts were used for the reconstruction of the alar lobule. However, the trial demonstrated significant variability in the histological and biochemical measures of quality (i.e., Bern score; an histological grade of neocartilage tissue quality, 0-9 min to max scale and GAG/DNA) of the grafts between donors. These quality metrics focus on the characteristics of the ECM of nasal cartilage deposited in the grafts.

There is thus still a need to be provided with a means to produce high-quality engineered nasal cartilage for graft.

SUMMARY

It is provided a method of producing a cartilage graft comprising expanding autologous chondrocytes and/or chondroprogenitors) from a donor patient, selecting expanded chondrocytes and/or chondroprogenitors by detecting the expression of at least one surfaceome protein gene or secretome protein gene, and culturing the selected expanded chondrocytes and/or chondroprogenitors in a culture medium allowing formation of a transplantable cartilage material.

In an embodiment, the chondrocytes are of human or animal origin.

In another embodiment, the chondrocytes are ear chondrocytes, nasal chondrocytes, rib chondrocytes, or knee chondrocytes.

In an embodiment, the chondrocytes are human nasoseptal chondrocytes (hNC) or human sternal chondrocytes.

It is further provided a kit for selecting chondrocytes to produce high-quality transplantable cartilage material comprising at least one probe for detecting at least one surfaceome protein gene or secretome protein gene; and instruction for use.

In an embodiment, the selected chondrocytes and/or chondroprogenitors are cultured in a 3D culture.

In a further embodiment, the selected chondrocytes and/or chondroprogenitors are co-cultured with mesenchymal stem cells (MSC).

In an embodiment, the MSC are from bone marrow, adipose, synovium, synovial fluid, and from other anatomical sites.

In a further embodiment, the MSC are FGF2-expanded human bone marrow mesenchymal stem cells (hBMMSC).

In an embodiment, the culture medium comprises at least one of fibroblast growth factor 2 (FGF-2) and transforming growth factor beta-1 (TGFβ1).

In a further embodiment, the culture medium comprises FGF-2 and TGFβ1 (T1F2).

In an embodiment, the at least one surfaceome protein gene is ADGRG1, NPR3, SLC16A4, TSPAN13, FZD4 and SLC22A23.

In a further embodiment, the at least one secretome protein gene is ADGRG1, B3GNT7, COLGALT2, IGFBP3, STC2, SAA1, ANGPLT1, COL8A2, INHBB, ADAMTS9, ORM1, COL14A1, DCN, COL21A1, ENOX1, IL7, MXRA5 GAL, TFRC, SERPINA9, LIF, GDF6 and COL5A3.

In an embodiment, the expression of at least one secretome protein gene of ADGRG1, NPR3, SLC16A4, TSPAN13, ADGRG1, B3GNT7, COLGALT2, IGFBP3, STC2, SAA1, ANGPLT1, COL8A2, INHBB, ADAMTS9, ORM1, COL14A1 and DCN is indicative of high-quality of transplantable nasal cartilage material.

In a further embodiment, the expression of at least one of FZD4, SLC22A23, COL21A1, ENOX1, IL7, MXRA5 GAL, TFRC, SERPINA9, LIF, GDF6, COL5A3 DCN is indicative of poor-quality of transplantable cartilage material.

In an embodiment, the expression of at least one surfaceome protein gene or secretome protein gene is detected by measuring the coded mRNA or encoded protein.

In a further embodiment, the expression of the at least one surfaceome protein gene or secretome protein gene is detected by using a probe.

In an embodiment, the expression of the at least one surfaceome protein gene or secretome protein gene is detected by using a nucleic acid probe or an antibody.

In a further embodiment, the transplantable cartilage material is a nasal cartilage material.

In another embodiment, the donor patient is a human or an animal.

It is also provided a kit for selecting chondrocytes or chondroprogenitors to produce high-quality transplantable cartilage material comprising at least one probe for detecting at least one surfaceome protein gene or secretome protein gene and instruction for use.

In an embodiment, the kit encompassed further comprises a culture medium.

In an embodiment, the probe detects the coded mRNA or encoded protein expression of the at least one surfaceome protein gene or secretome protein gene.

In another embodiment, the probe is a nucleic acid probe or an antibody.

BRIEF DESCRIPTION OF THE DRAWINGS

Reference will now be made to the accompanying drawings.

Figure 12:
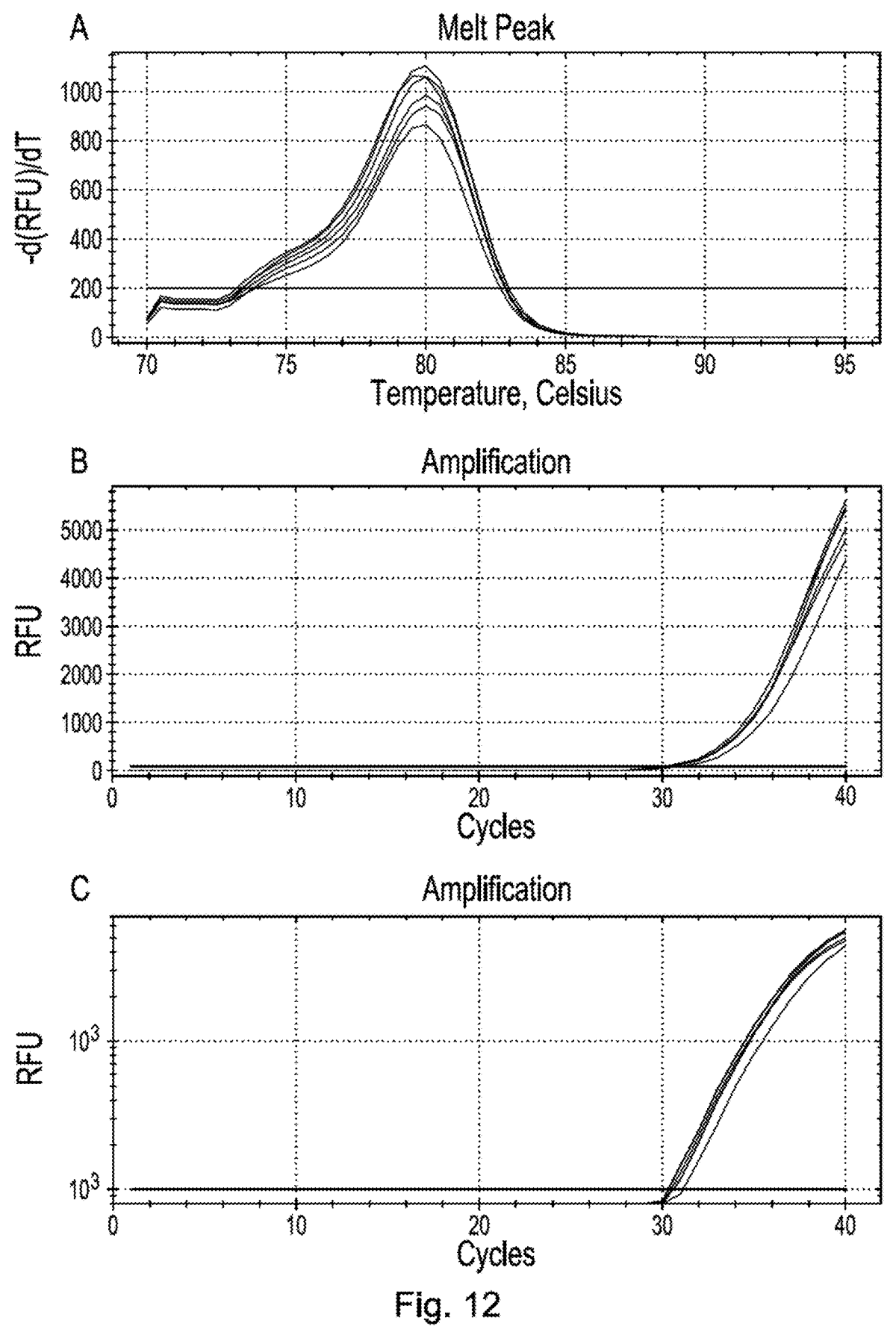

FIG. 12 illustrates in (A) melting curve profile of horse YWHAZ (tyrosine 3-monooxygenase/tryptophan 5-monooxygenase activation protein zeta; accession: XM_014728222.2) after 40 cycles of qPCR run of cDNA developed from total RNA of primary horse nasal septal chondrocytes in monolayer culture; wherein in (B) and (C) represent non-log 10 and log 10 transformed qPCR profiles of YWHAZ, respectively.

DETAILED DESCRIPTION

Figure 1:
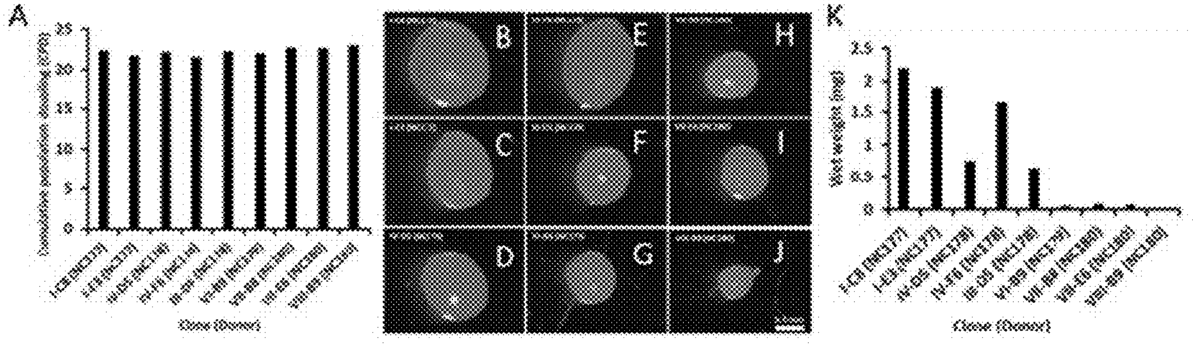
FIG. 1 illustrates in (A) cumulative cell population doubling of clonal hNC from multiple donors; in B-J gross appearance of clonal hNC-derived pellets from four donors after 3 weeks of chondrogenic culture of 500,000 clonal hNC per pellet, wherein clone (donor) are (B): I-C8 (NC177); (C): I-E3 (NC177); (D): IV-D5 (NC178); (E): IV-F6 (NC178); (F): III-D5 (NC178); (G): VI-B9 (NC179); (H): VII-B8 (NC180); (I): VII-E6 (NC180); (J): VIII-B9 (NC180); and in (K) wet weight (WW) of hNC clonal pellets.

It is provided a method of selecting and producing high-quality engineered cartilage graft.

Accordingly, as reported in Table 1, a novel panel of four (4) surfaceome encoding genes: ADGRG1, NPR3, SLC16A4 & TSPAN13, that correlate with high-quality engineered cartilage forming hNC. In addition, two (2) novel surfaceome encoding genes were identified: FZD4 & SLC22A23, that correlate with poor-quality engineered cartilage. A novel panel of thirteen (13) secretome encoding genes was identified: ADGRG1, B3GNT7, COLGALT2, IGFBP3, STC2, SAA1, ANGPLT1, COL8A2, INHBB, ADAMTS9, ORM1, COL14A1 and DCN that correlate with high-quality engineered cartilage forming hNC. Finally, ten (10) novel secretome encoding genes were identified: COL21A1, ENOX1, IL7, MXRA5 GAL, TFRC, SERPINA9, LIF, GDF6 & COL5A3, that correlate with poor-quality engineered cartilage forming hNC.

TABLE 1

Summary of novel marker genes of high- and poor-quality engineered cartilage

| Gene Symbol | Cell surface proteins (surfaceome) | Cartilage quality |
|---|---|---|
| ADGRG1 | G-protein coupled receptor 56 | High |
| NPR3 | Atrial natriuretic peptide receptor 3 | High |
| SLC16A4 | Monocarboxylate transporter 5 | High |
| TSPAN13 | Tetraspanin-13 | High |
| FZD4 | Frizzled 4 | Poor |
| SLC22A23 | Solute carrier family 22- member 23 | Poor |
| | Secreted proteins (secretome) | |
| ADGRG1 | G-protein coupled receptor 56 | High |
| B3GNT7 | UDP-GlcNAc:betaGal beta-1,3-N-acetylglucosaminyltransferase 7 | High |
| COLGALT2 | Collagen Beta (1-O) Galactosyltransferase 2 | High |
| IGFBP3 | Insulin-like growth factor-binding protein 3 | High |
| STC2 | Stanniocalcin-2 | High |
| SAA1 | Serum amyloid A1 | High |
| ANGPLT1 | Angiopoietin 1 | High |
| COL8A2 | Collagen Type VIII Alpha 2 | High |
| INHBB | Inhibin Subunit Beta B | High |
| ADAMTS9 | A disintegrin and metalloproteinase with thrombospondin motifs 9 | High |
| ORM1 | Orosomucoid 1 | High |
| COL14A1 | Collagen Type XIV Alpha 1 Chain | High |
| DCN | Decorin | High |
| COL21A1 | Collagen Type XXI Alpha 1 | Poor |
| ENOX1 | Ecto-NOX Disulfide-Thiol Exchanger 1 | Poor |
| IL7 | Interleukin-7 | Poor |
| MXRA5 | Matrix Remodeling Associated 5 | Poor |
| GAL | Galanin | Poor |
| TFRC | Transferrin Receptor | Poor |
| SERPINA9 | Serpin Family A Member 9 | Poor |
| LIF | LIF Interleukin 6 Family Cytokine | Poor |
| GDF6 | Growth Differentiation Factor 6 | Poor |
| COL5A3 | Collagen alpha 3(V) | Poor |

It has been demonstrated that direct coculture of mesenchymal stem cells (MSC) including FGF2-expanded human bone marrow mesenchymal stem cells (hBMMSC) with either articular chondrocytes or hNC result in a synergistic production of GAG matrix. The synergism as intended herein encompass chondroinduction, where the amount of GAG matrix produced is more than would be expected from the individual contributions of the pure chondrocytes and pure MSC. The coculture approach can mitigate the donor-donor variability in engineered nasal cartilage graft quality between hNC donors. While coculture of hNC and hBMMSC is a promising strategy to augment the quality of engineered nasal cartilage grafts, the reality is that without pretreatment of the engineered graft with parathyroid hormone related peptide (PTHrP) to suppress hypertrophic chondrogenesis of the hBMMSC, the engineered graft will undergo modifications akin to endochondral ossification after subcutaneous implantation. Moreover, while it is known that FGF2 maintains the chondrogenic potential of hBMMSC during long-term expansion, it is unknown if strategies to mitigate the propensity of hBMMSC to undergo hypertrophic chondrogenesis without the loss of chondrogenic potential such as hypoxic culture and combined FGF2 and WNT3A, would have any negative impact on chondroinduction between hNC and hBMMSC. And more importantly, it is unknown if the combined presence of hypoxia, FGF2 and WNT3A during long-term expansion of hBMMSC nullify the propensity of cocultured hBMMSC to undergo endochondral ossification in vivo without PTHrP pretreatment.

Engineered articular and nasal cartilage vary highly in quality; defined by GAG/DNA and Bern score. Grogan et al. (2007, Arthritis Rheum, 56: 586-595) conducted microarrays on microtissue pellets of human articular chondrocytes (hAC) of low or high chondrogenic capacity and determined that high chondrogenic capacity hAC expressed CD49c, CD49f, CD44 and CD151. Low-chondrogenic capacity hAC expressed higher levels of IGF-1, MMP2 and ADAMTS-5. In a study of femoral condyle articular chondrocyte progenitors (ACP) from 4 healthy male human donors (age 26-33), it was identified that the expression of ACAN was upregulated in high chondrogenic cells. This was true between donors and between autologous ACP clones.

The advent of low-cost 3D printers has enabled significant and increasing exploratory work in their use for the biofabrication of engineered cartilage. And with the increasing availability of new polymers, "bioinks," and advances in printability of naturally occurring cartilage suitable polymers such as type I collagen- and hyaluronan-based hydrogels, this trend will continue. The opportunity to fabricate suturable compliant custom shaped human nasal cartilage grafts with high-fidelity through 3D bioprinting can positively impact nasal cartilage reconstructive surgeries and mitigate/eradicate donor site morbidities because of harvesting autologous cartilage grafts from other anatomical sites. To date, no study has focused on bioprinting of suturable custom shaped human nasal cartilage grafts for use in reconstructive surgeries.

It is known that the quality of engineered nasal cartilage can be enhanced by coculture of hBMMSC with T1F2-expanded hNC without the risk of the hBMMSC component undergoing endochondral ossification in vivo by pretreatment with PTHrP. Accordingly, coculture of hBMMSC and hNC reduces the donor-donor variability in engineered cartilage grafts. Furthermore, higher cell plating density of hNC prior to cell culture expansion enhances the quality of the engineered cartilage graft. Moreover, using an 80-protein array, a panel of soluble factors were identified that negatively impact the quality of engineered cartilage from cocultured hBMMSC and hNC. A 3D bioprinting was used to fabricate custom-shaped high-quality, and high-fidelity engineered cartilage grafts from hNC-laden collagen I hydrogel.

Figure 2:
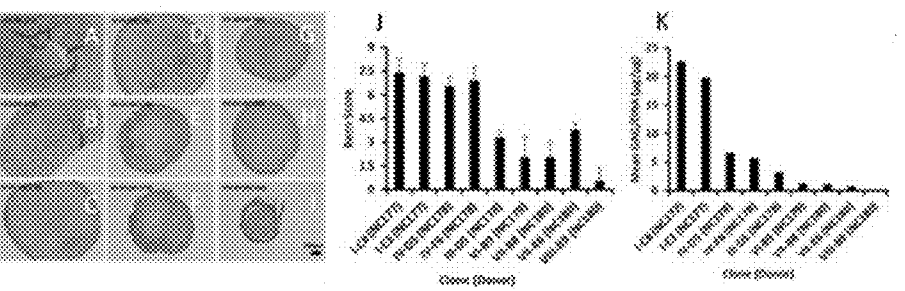
FIG. 2 illustrates safranin O histology and Bern scoring of clonal hNC-derived pellets from four donors after 3 weeks of chondrogenic wherein clone (donor) are (A): I-C8 (NC177); (B): I-E3 (NC177); (C): IV-D5 (NC178); (D): IV-F6 (NC178); (E): III-D5 (NC178); (F): VI-B9 (NC179); (G): VII-B8 (NC180); (H): VII-E6 (NC180); (I): VIII-B9 (NC180); in (J) histological scoring of engineered neocartilage quality via Bern Score (min-max; 0-9 scale) of microtissues engineered from hNC clone from 4 donor, where Bern score±standard deviation from 4 blinded observers; and in (K) mean GAG/DNA of duplicate microtissues developed from 4 donors' clonal hNC.
Figure 3:
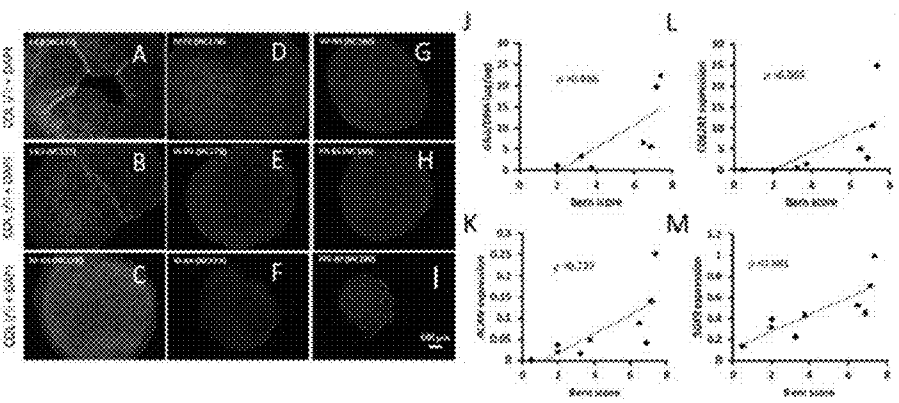
FIG. 3 illustrates the immunofluorescence (IF) image of human collagen I, collagen II and nuclei (DAPI) in nasal cartilage microtissue pellets from clonal-derived hNC wherein clone (donor) are (A): I-C8 (NC177); (B): I-E3 (NC177); (C): IV-D5 (NC178); (D): IV-F6 (NC178); (E): III-D5 (NC178); (F): VI-B9 (NC179); (G): VII-B8 (NC180); (H): VII-E6 (NC180); (I): VIII-B9 (NC180); and GAG/DNA content and gene expression correlation with Bern score is shown in (J): mean GAG/DNA vs Bern score; and (K): ACAN expression vs Bern score; L. COL2A1 expression vs. Bern score; M. SOX9 expression vs Bern score.

In an attempt to better understand the characteristics of hNC that develop to good- or bad-quality engineered nasal cartilage, clonal populations of hNC was developed by serial dilution of hNC isolated from the four donors (two females (NC177, 27 years; NC180, 24 years) and two males (NC178, 23 years; NC179, 36 years) followed by in vitro cell expansion in the presence of T1F2 to develop a clonal bank of hNC. A total of 9 clones were randomly selected from each donor for further investigation. The cumulative population doubling (CPD) of the selected clones were recorded (FIG. 1A). Three-dimensional (3D) cell pellet model for cartilage formation were set up from the selected clones at 0.25 million hNC per pellet. A total of 10 pellets per selected clone were set up and the matching hNC of each of the selected clones were stored at −80° C. for RNA-Sequencing (RNASeq). After 3 weeks of pellet culture in chondrogenic media, the resulting cartilage microtissues were: 1) photographed for gross appearance (FIGS. 1B-J), weighed (FIG. 1K); 2) assessed histologically for cartilaginous ECM synthesis by Safranin O dye (FIGS. 2A-4I); 3) evaluated for neocartilage quality by four blinded observers via the Bern score ranged from 0.5-7.5 in the microtissue pellets with the best clonal-derived microtissues approaching normal nasoseptal cartilage (FIG. 2J); 4) evaluated for GAG/DNA content ratio as a metric for cartilage quality (FIG. 2K); and 5) subjected to types I and II collagen immunofluorescence (IF) as ECM components of nasoseptal cartilage (FIGS. 3A-I). Furthermore, gene expression analyses were performed via qPCR to assess chondrocyte phenotype ACAN, COL1A2, COL2A1, type X COL10A1, and SOX9. Bern score strongly correlated with wet weight (Spearman's $\rho=0.913$; $p<0.0001$), GAG ($\rho=0.884$; $p<0.0001$), DNA ($\rho=0.753$; $p<0.0001$), GAG/DNA ($\rho=0.866$; $p<0.0001$; FIG. 3J), ACAN ($\rho=0.777$; $p<0.0001$; FIG. 3K), COL2A1 ($\rho=0.903$; $p<0.0001$; FIG. 3L) and SOX9 ($\rho=0.681$; $p<0.0001$; FIG. 3M). In contrast, there was a negative correlation between Bern score and CPD ($\rho=-0.358$; $p<0.05$). Bern score and COL10A1 (a marker of hypertrophic chondrocytes) correlated negatively but non-significantly ($\rho=-0.116$; $p=0.351$). Based on the Bern score and expression of cartilage-specific type II collagen, 4 hNC clones were identified from 2 donors (i.e., I-C8 (NC177); I-E3 (NC177); IV-D5 (NC178) & IV-F6 (NC178)) that produced good-quality nasal cartilage microtissues, and 5 hNC clones from 3 donors (i.e., III-D5 (NC178); VI-B9 (NC179); VII-B8 (NC180); VII-E6 (NC180) & VIII-B9 (NC180)) that produced bad-quality microtissues.

Figure 4:
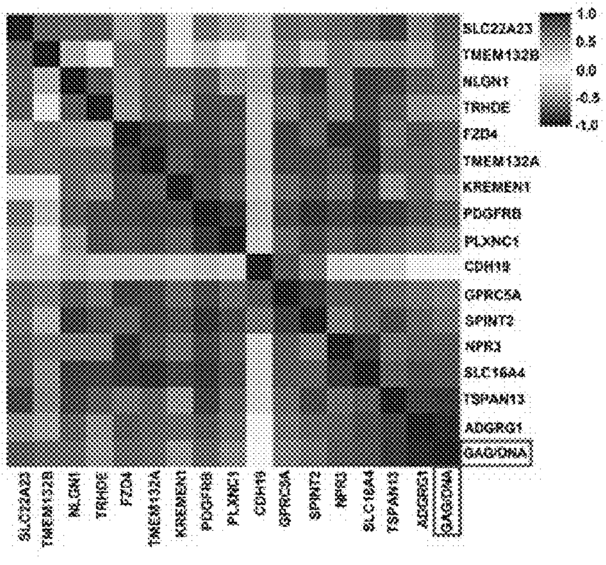
FIG. 4 illustrates a correlation heatmap of the 16 genes identified from surfaceome query of 'Good' vs 'Bad' hNC with GAG/DNA.
Figure 5:
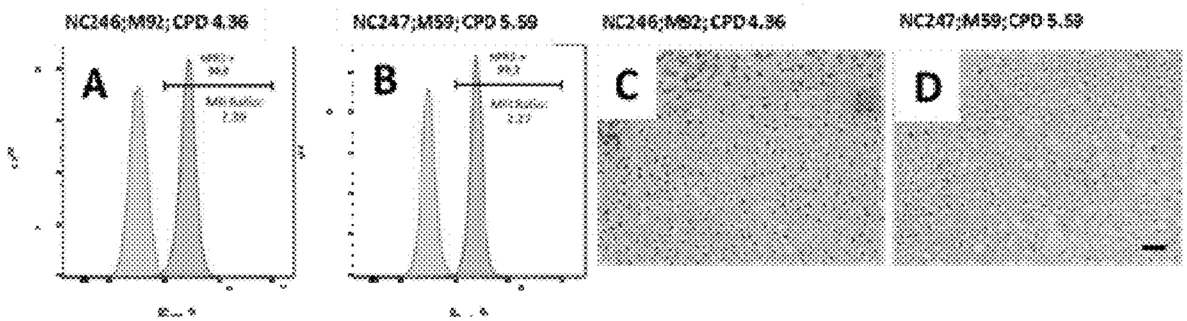
FIG. 5 illustrates an anti-NPR3 flow cytometry of hNC from: (A): NC246 (Male 92, CPD=4.36); (B): NC247 (Male 59, CPD=5.59); and safranin O staining of hNC pellets (C): NC246; (D): NC247.

RNASeq were performed on the matching stored hNC of the selected clones that had been previously stored in −80° C., to ultimately identify genes encoding cell surface proteins to discriminate between hNC producing good- and bad-quality engineered nasal cartilage. After running a standard preprocessing pipeline of the raw RNASeq reads and normalization of the gene counts using Partek Flow software, a total of 12,980 genes were included for differential expression analysis with ANOVA. Comparisons were made between the good (n=4) and bad (n=5) hNC clones. A total of 56 genes were identified with Fold Change (FC)≥3 (q value ≤0.05; $p<0.05$) in their expression between the "good" and "bad" clonal hNC (FIG. 4). An in silico surfaceome was used (public resource with capacity to filter multiomics data) to uncover cell-surface protein encoding genes. The surfaceome query generated a total of 16 genes. A total of 4 genes (i.e., ADGRG1, NPR3, SLC16A4 & TSPAN13) from the 16 correlated significantly (Pearson's $r\geq0.78$; $p<0.05$) with the GAG/DNA of the corresponding microtissues (FIG. 4). A total of 2 genes (i.e., FZD4 and SLC22A23) from the 16 were inversely correlated (Pearson's $r\geq-0.68$; $p<0.05$) with GAG/DNA of the microtissues (FIG. 4). A validation exercise was then performed for NPR3 which had the least positive correlation coefficient (i.e., Pearson's $r=0.78$; $p=0.01$) with GAG/DNA. For the validation, hNC from two male patients (age 59 & 92 years) were tested with basal cell carcinoma, a type of NMSC, undergoing nasal reconstructive surgeries. Flow cytometry with fluorescent labeled anti-NPR3 showed that ≥98% of the hNC from both patients were positive for NPR3 (i.e., Natriuretic Peptide Receptor 3) after >4 CPD with T1F2 (FIGS. 5A and B). Furthermore, the hNC formed safranin O positive microtissues after 3 weeks of pellet culture in chondrogenic media (FIGS. 5C and D). The microtissue from the 92 y/o had a GAG/DNA of 12.2±0.73 μg/μg, and the 59 y/o had a GAG/DNA of 16.6±4.69 μg/μg. The expression of ADGRG1, NPR3, SLC16A4 & TSPAN13 was also validated to be significantly higher in the good cartilage by qPCR.

As encompassed herein, surfaceome proteins are understood to correspond to cell surface exposed proteins.

As encompassed herein, expression of genes can be measured using probes, such as a nucleic acid probe or an antibody, in order to detect the coded mRNA or encoded protein.

Figure 6:
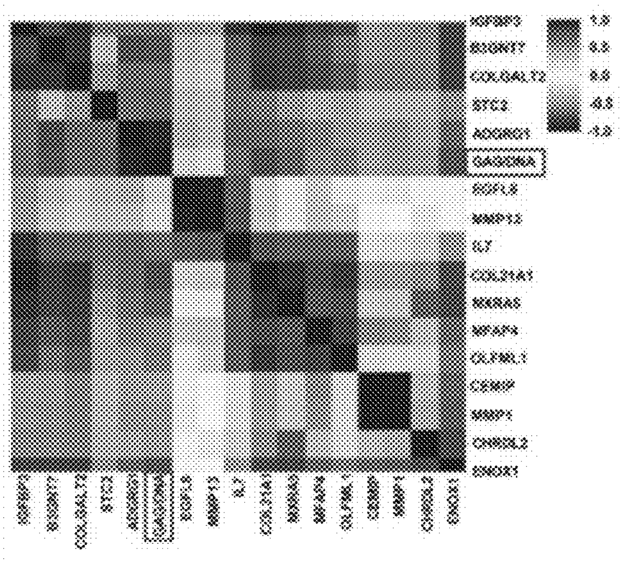
FIG. 6 illustrates the correlation heatmap of the 16 genes identified from secretome query of 'Good' vs 'Bad' hNC with GAG/DNA.

In an attempt to determine if the good- and bad-quality producing engineered nasal cartilage hNC secrete different proteins, the genes encoding proteins annotated as secreted (i.e., secretome) were selected from the list of significant genes (FC 2, q<0.05) by cross-matching with the revised list of the human secretome. Pearson correlation analysis was performed, and 16 genes correlated with GAG/DNA content. 5 secretome encoding genes were identified (i.e., ADGRG1, B3GNT7, COLGALT2, IGFBP3 & STC2) that positively correlated with GAG/DNA (Pearson's r≥0.67; p<0.05). And there were 4 other secretome encoding genes (i.e., COL21A1, ENOX1, IL7 & MXRA5) that inversely correlated with GAG/DNA (Pearson's r≥−0.65; p<0.05) (FIG. 6). It was reported that IL7 secretion to be inversely correlated with the GAG/DNA and Bern score of engineered human nasal cartilage. It is noteworthy, that ADGRG1 is both a surfaceome and secretome encoding gene. These panel of genes are unknown regarding cartilage quality.

Figure 7:
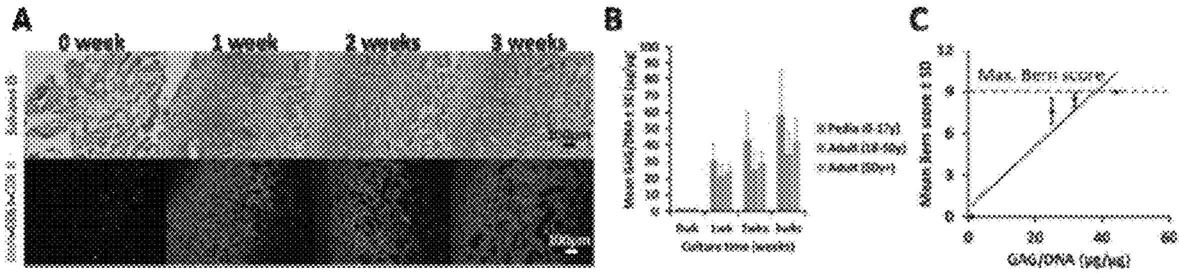
FIG. 7 illustrates in (A) fast green, Safranin O (pink), and hematoxylin staining showing the distribution of the collagen, GAG and cells, respectively (top panel), wherein immunofluorescence (IF) for collagen I (red), collagen II (green) and cell nuclei (DAPI; blue) (lower panel) in engineered nasal cartilage graft; in (B) GAG/DNA content of engineered nasal cartilage graft over a time course of 3-weeks of graft tissue development per three age groups of hNC donors (pediatric (pedia)=0-17 years; adult=18-50 years; adult=50 years+); in (C) pearson correlation between GAG/DNA and Bern score), wherein the images in (A) were acquired from grafts made of hNC' of a female (62 years), scale bar=100 μm.

Culture expanded autologous hNC were used to engineer cartilage grafts in a first of its kind clinical trial, involving two females and three males (aged 76-88 years) with NMSC on the nose (Fulco et al., 2014, Lancet, 384: 337-346). The grafts were formed after 4 weeks of the hNC culture in Chondro-Gide, a clinically approved porcine-derived type I and III collagen membrane scaffold. There was significant variability in the quality of grafts based on GAG/DNA and Safranin O staining. But it is unclear if variables such as: culture time, gender, age, and CPD could impact graft quality. The culture of hNC on Chondro-Gide was replicated to understand the in vitro development of engineered nasal cartilage graft and evaluated the impact of the variables on graft quality. Thus, the grafts generated on Chondro-Gide were studied from the time of seeding with hNC and at the end of each week for 3 weeks. hNC were isolated from 7 males (aged 8-52 years) and 5 females (aged 11-62 years) followed by expansion in T1F2 (i.e., TGFβ1 & FGF2) as in the clinical trial. Preliminary analyses by safranin O histology for sulfated GAG along with types I and II collagens as functional ECM of nasal cartilage (FIG. 7A), GAG/DNA (FIG. 7B), and Bern score (FIG. 7C; Pearson's r=0.79; $p=2\times10^{-7}$) as quality metrics revealed strong positive correlation with culture time (Pearson's r=0.89; $p=5.8\times10^{-11}$ with Bern score; Pearson's r=0.73; $p=5\times10^{-9}$ with GAG/DNA). Furthermore, there was no correlation between donor age of hNC and Bern score (Pearson's r=0.063; p=0.74) or GAG/DNA (Pearson's r=−0.206; p=0.16) of engineered tissue grafts. Similarly, there was no correlation between CPD and Bern score (Pearson's r=−0.255; p=0.18) or GAG/DNA (Pearson's r=−0.167; p=0.256). Moreover, there was no significant difference between the quality of engineered nasal cartilage developed from male and female hNC (not shown).

Given the significant positive correlation of Bern score or GAG/DNA with culture time, RNASeq were performed on graft tissue from the time of seeding hNC and at the end of each week for 3 weeks. A total of 24 engineered cartilage grafts developed from hNC donors were evaluated: three females (NC130, 11 years; NC140, 62 years; NC148, 29 years) and three males (NC131, 14 years; NC133, 28 years; NC138, 52 years). After running a standard preprocessing pipeline of the raw RNA sequencing reads and normalization of the gene counts as described previously using Partek Flow software (Szojka et al., 2021, Journal of Tissue Engineering, 12), a total of 13,373 genes were included for differential expression analysis with ANOVA. Three expression level comparisons were made between 0 week and the following time points: 1 week, 2 weeks and 3 weeks. The comparisons resulted in a total of 803 genes (q≤0.05, p<0.05, FC≥5). With the rationale to identify secreted soluble proteins in culture media that highly correlate with the quality of engineered nasal cartilage during in vitro development, a cross-matching analysis was performed of the 803 genes with the revised list of the human secretome. 181 genes were identified as encoding proteins annotated as secreted. A Pearson correlation analyses was performed between the 181 genes and the GAG/DNA of the grafts. A total of 149 genes correlated with GAG/DNA. By selecting genes that significantly correlated (i.e., Pearson's r≥0.8 or −0.8; p<0.05), a total of 14 secretome annotated genes were identified. There were 8 genes (i.e., SAA1, ANGPLT1, COL8A2, INHBB, ADAMTS9, ORM1, COL14A1 & DCN) that positively (Pearson's r≥0.90; p<0.05) correlated with GAG/DNA. The remaining 6 genes (i.e., GAL, TFRC, SERPINA9, LIF, GDF6 & COL5A3) inversely correlated with GAG/DNA. Some of these secretome annotated genes encode for proteins that either become incorporated in the ECM or in the cell membranes (i.e., COL5A3, COL8A2, COL14A1, DCN and TFRC). To that end, a cohort known to encode for unbound and soluble proteins was selected (e.g., SAA1, ANGPLT1) to monitor in vitro development of engineered cartilage.

Figure 8:
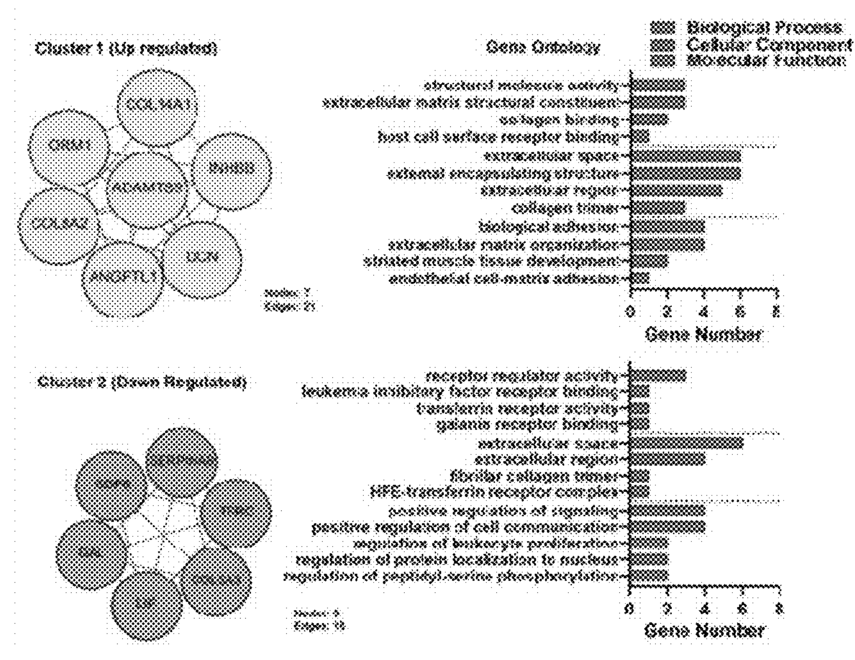
FIG. 8 illustrates the gene correlation network (GCN) and gene ontology analysis outcome of identified secretome annotated genes during the time course of engineered nasal cartilage development.
Figure 9:
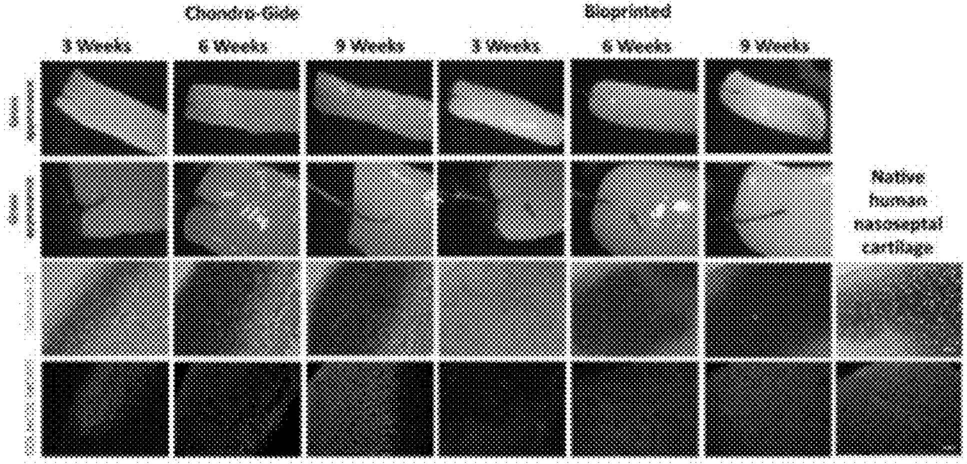
FIG. 9 illustrates gross appearance of engineered nasal cartilage graft (top two panels) after 3, 6 and 9 weeks of culture; Fast green, safranin O and hematoxylin staining showing the distribution of the collagen, GAG, and cells in Chondro-Gide and bioprinted grafts, and native nasoseptal cartilages, respectively (third panel down); immunofluorescence images for collagen I, collagen II and cell nuclei in Chondro-Gide and bioprinted grafts, and native nasoseptal cartilages, respectively (bottom panel), wherein arrows on 3 & 6 weeks of "bioprinted" gross appearance images indicate surgical sutures slicing through the bioprinted graft, and wherein scale bar 100 μm.
Figure 10:
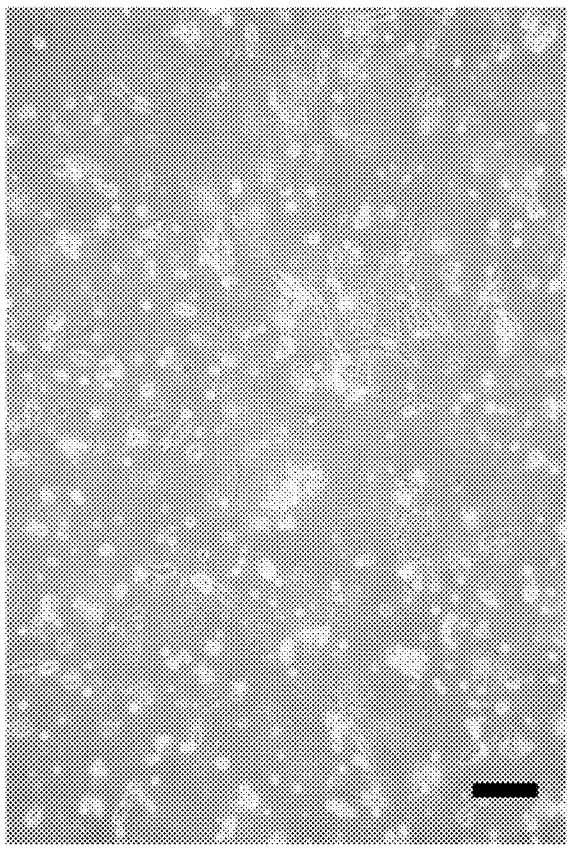
FIG. 10 illustrates a light microscopy phase contrast image of the primary horse nasal septal chondrocytes in monolayer plastic-adherent cell culture after 48 hours of recovery post collagenase (i.e., type II collagenase; 0.15% w/v of 300 units/mg; Worthington) mediated isolation via digestion of horse nasal septum cartilage in high glucose Dulbecco's modified Eagle's medium (HG-DMEM) supplemented with 10% v/v heat-inactivated horse serum (HS), 10 mM 4-(2-hydroxyethyl)-1-piperazineethanesulfonic acid (HEPES), 100 U/mL penicillin, 100 μg/ml streptomycin and 2 mM L-glutamine. Scale bar=100 μm.
Figure 11:
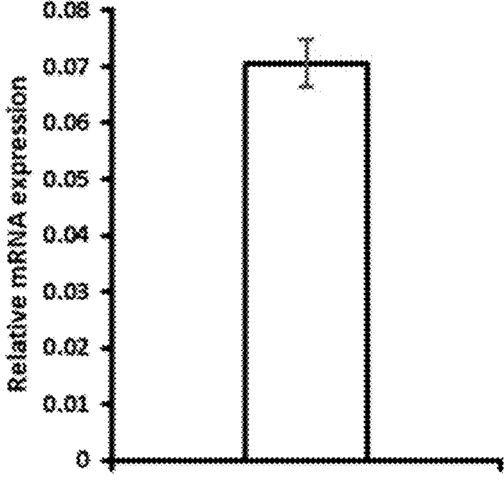
FIG. 11 illustrates relative mRNA expression of horse ADGRG1 (Accession: XM_023637057.1) in horse nasal septal chondrocytes in monolayer culture via quantitative polymerase chain reaction (qPCR). The three reference or housekeeping genes that were used for normalization of horse ADGRG1 mRNA expression were horse: YWHAZ (tyrosine 3-monooxygenase/tryptophan 5-monooxygenase activation protein zeta; accession: XM_014728222.2), ACTB (beta actin; accession: NM_001081838.1) and B2M (beta-2-microglobulin; accession: NM_001082502.3).
Figure 13:
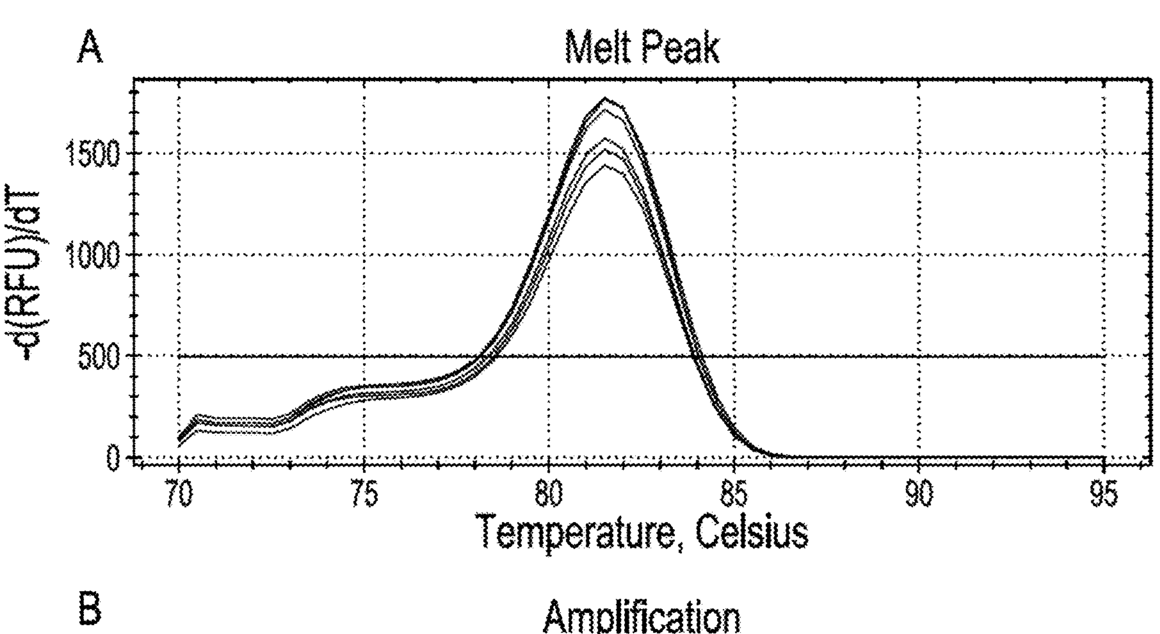
FIG. 13 illustrates in (A) melting curve profile of horse ACTB (beta actin; accession: NM_001081838.1) after 40 cycles of qPCR run of cDNA developed from total RNA of primary horse nasal septal chondrocytes in monolayer culture; wherein in (B) and (C) represent non-log 10 and log 10 transformed qPCR profiles of ACTB, respectively.
Figure 13:
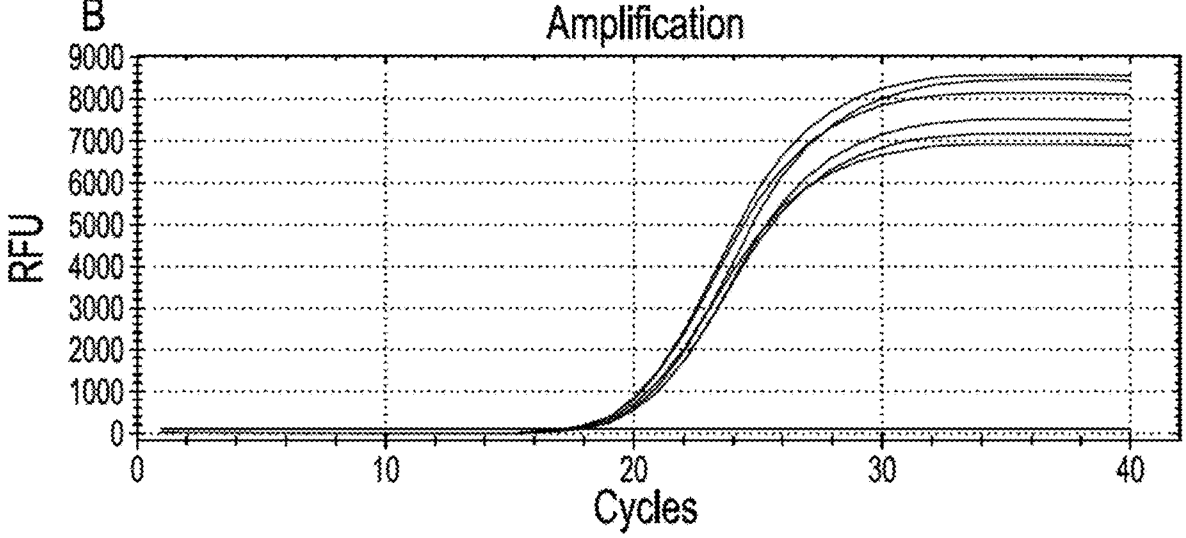
Figure 13:
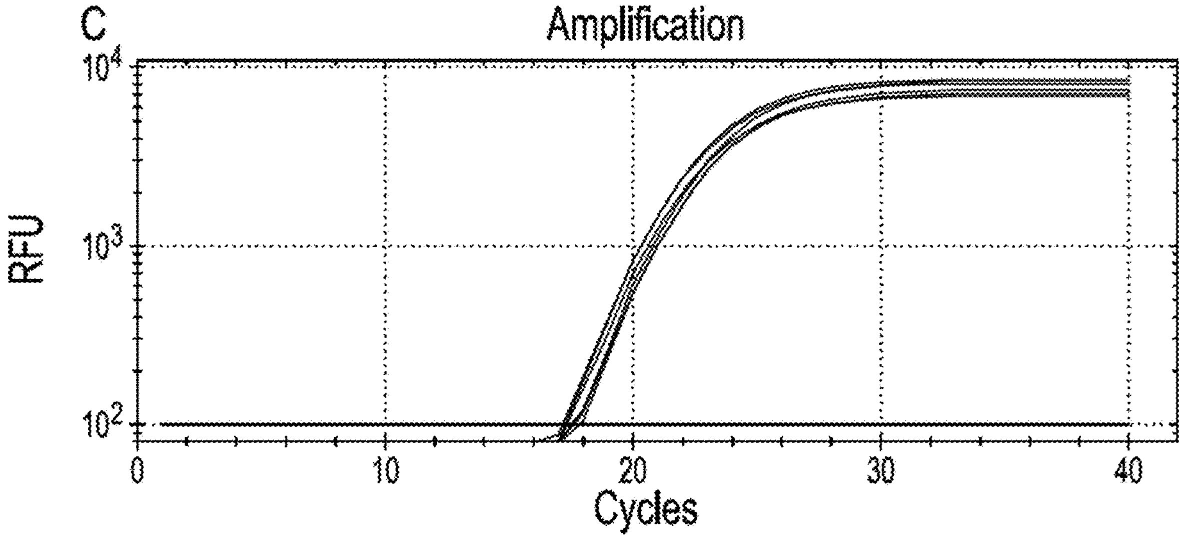
Figure 14:
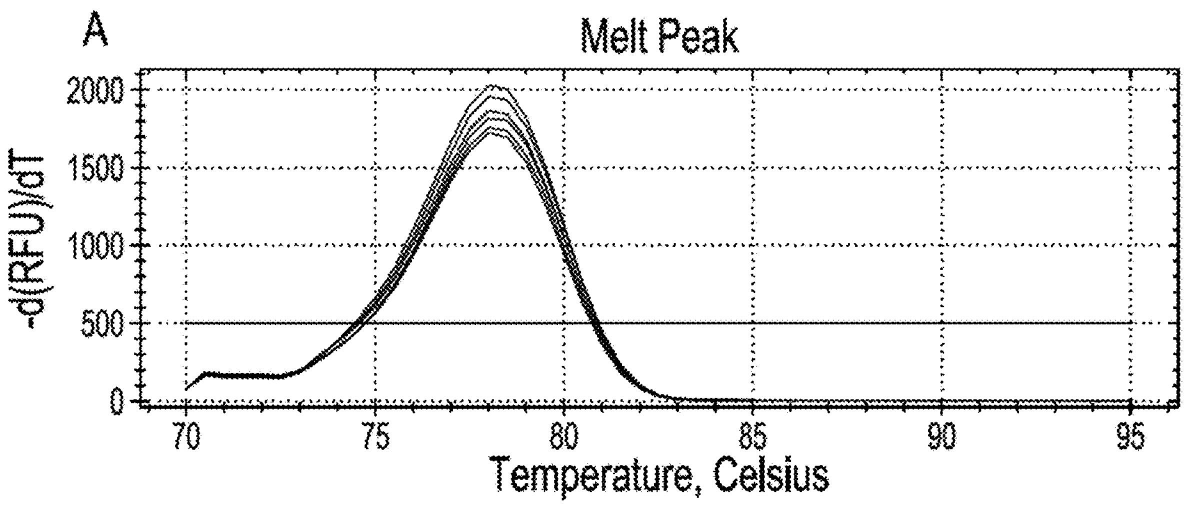
FIG. 14 illustrates in (A) melting curve profile of horse B2M (beta-2-microglobulin; accession: NM_001082502.3) after 40 cycles of qPCR run of cDNA developed from total RNA of primary horse nasal septal chondrocytes in monolayer culture; wherein in (B) and (C) represent non-log 10 and log 10 transformed qPCR profiles of B2M, respectively.
Figure 14:
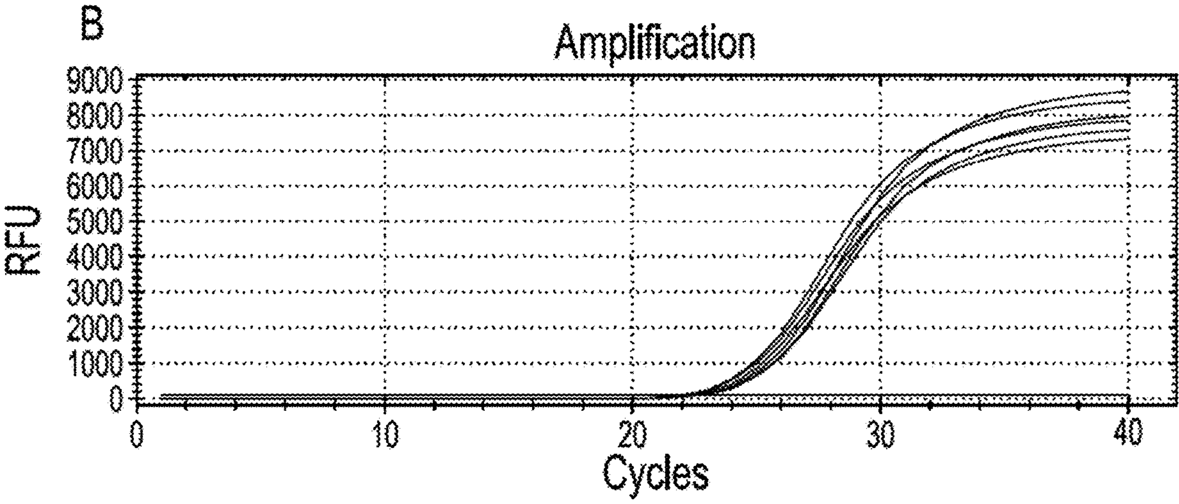
Figure 14:
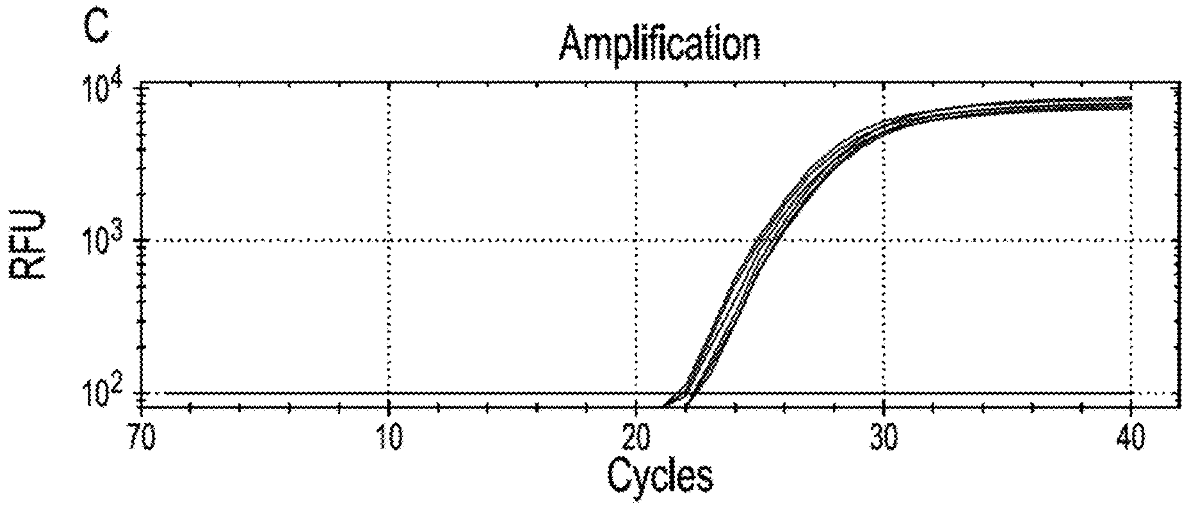
Figure 15:
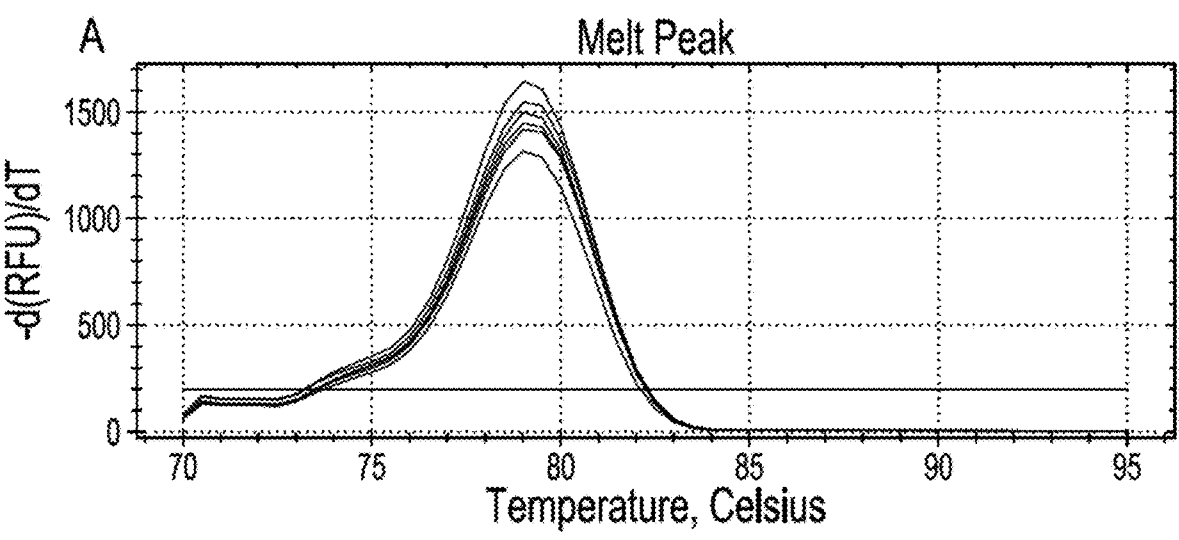
FIG. 15 illustrates in (A) melting curve profile of horse ADGRG1 (Accession: XM_023637057.1) after 40 cycles of qPCR run of cDNA developed from total RNA of primary horse nasal septal chondrocytes in monolayer culture; wherein in (B) and (C) represent non-log 10 and log 10 transformed qPCR profiles of ADGRG1, respectively.
Figure 15:
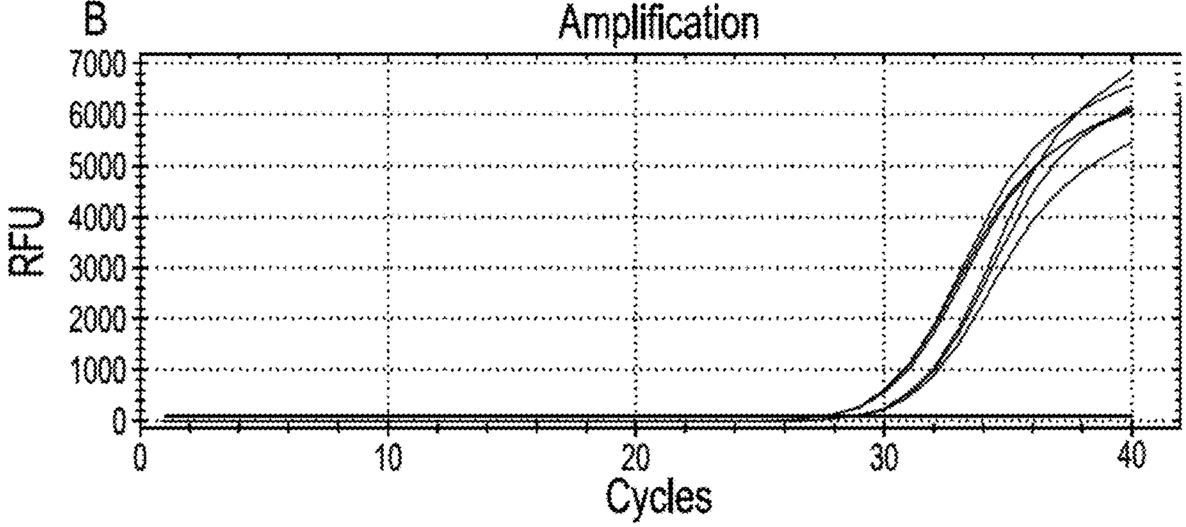
Figure 15:
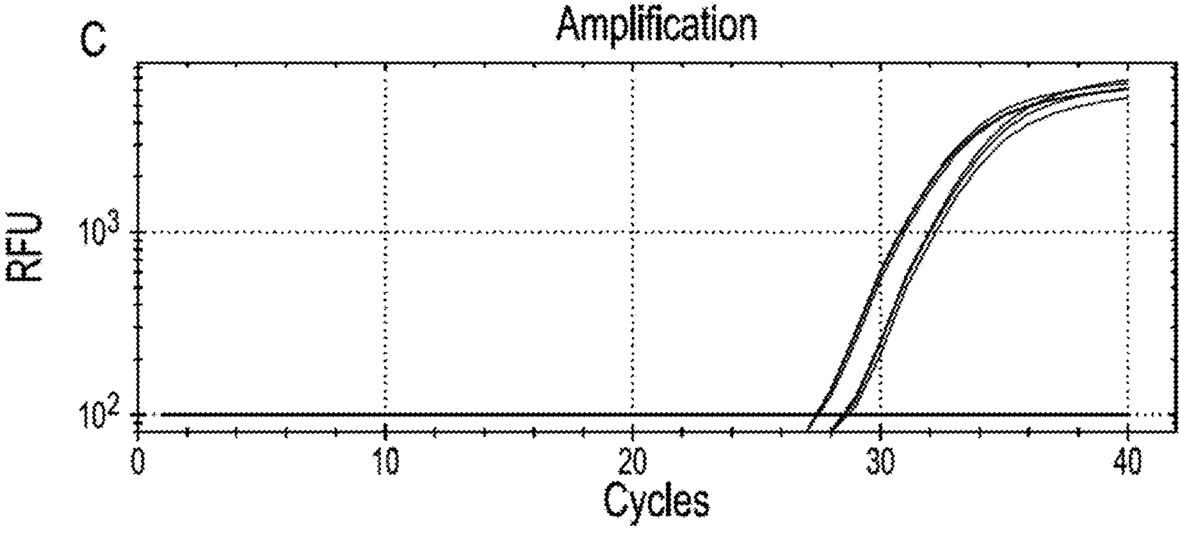

To get an understanding of the possible signaling pathways that the 14 identified secretome annotated genes are associated with during in vitro development of the engineered nasal cartilage, a Kyoto Encyclopedia of Genes and Genomes (KEGG) pathway analysis was performed. The analysis showed four of the secretome annotated genes (DCN, INHBB, GDF6 & LIF) as significantly modulated (FC≥2, q≤0.05; p<0.001) and associated with TGFβ signaling and pathways regulating pluripotency of stem cells. As DCN and INHBB are positively correlated with GAG/DNA and culture time, and GDF6 and LIF are negatively correlated with GAG/DNA and culture time, their encoded proteins were proposed as strong candidate analytes to monitor the in vitro development of nasal cartilage grafts. To understand the biological processes that the 14 panel of secretome annotated genes are involved in, GCN analysis was sequentially performed by uploading the genes into a network analysis tool, Graphia, to generate cluster of genes exhibiting highly significant co-expression patterns followed by Gene Ontology (GO) analysis. Finally, the GO terms was summarized in REVIGO—an algorithm to reduce redundancy within generated lists of GO terms. GCN revealed two clusters of co-expressed genes from the 14 panel of secretome annotated genes: Cluster 1 (7 upregulated genes: ANGPLT1, COL8A2, INHBB, ADAMTS9, ORM1, COL14A1 & DCN) and Cluster 2 (6 downregulated genes: GAL, TFRC, SERPINA9, LIF, GDF6&COL5A3) (FIG. 8). REVIGO revealed that most of the genes in the GCN clusters are involved in biological processes of the extracellular matrix (FIG. 9). SAA1 was absent in the clusters. However, it has been implicated in matrix remodeling of articular cartilage.

3D Bioprinting offers the opportunity to engineer cartilage with custom geometries and sizes with high fidelity and without the inhomogeneous distribution of cartilage ECM as seen with Chondro-Gide. Therefore, bioprinting was explored and successfully engineered grafts from hNC in bovine-derived type I collagen hydrogel. However, the bioprinted grafts were unable to hold surgical sutures even after 6 weeks of in vitro culture relative to 3 weeks of grafts via Chondro-Gide (FIG. 9). 9 weeks of culture enabled the bioprinted graft to mature and hold surgical sutures (FIG. 9). Interestingly, at each time point, there was no difference between the GAG/DNA of Chondro-Gide and bioprinted engineered grafts. The flexural properties of the engineered grafts were measured, and performed Pearson correlation with culture time, and GAG/DNA. The bending moduli of the bioprinted and Chondro-Gide grafts correlated positively with culture time and GAG/DNA.

Accordingly, it is provided a means of producing a nasal cartilage graft comprising expanding autologous human nasoseptal chondrocytes (hNC) from a donor patient and selecting expanded hNC by detecting the expression of at least one surfaceome protein gene or secretome protein gene as described herein in order to culture selected expanded hNC in a culture medium allowing formation of a high-quality transplantable nasal cartilage material.

High-quality transplantable cartilage material encompasses cartilage material that expresses the functional extra-cellular matrix of cartilage along with exhibiting mechanical integrity needed for surgical transplantation.

It is thus provided that cartilage lacks blood supply. Its repair when injured requires transplantation or implantation of cells with good cartilage-forming ability. The discovered marker genes encoding the cell surface proteins of cells with high-quality or poor-quality cartilage-forming provides a means for cell-based cartilage therapies in veterinary and clinical medicine.

Over expression or knockdown of the discovered marker genes will allow therapeutically benefice in the treatment of cartilage and bone disorders in clinical and veterinary medicine. Such disorders include osteoarthritis, osteochondritis dissecans, and non-union bone fractures. The majority of bone in animals and human are formed through a cartilage intermediate. Therefore, the discovered cell surface protein encoding genes/proteins are anticipated to have utility in the treatment of bone disorders.

The discovered cell surface encoding genes/proteins are anticipated to have utility in the development of genetic/lab tests for cartilage and bone associated disorders both in veterinary and clinical medicine.

The marker proteins associated with the discovered cell surface protein encoding genes can be used in the manufacture of antibodies for the separation and stratification of cells with good or bad cartilage forming capacity. Biotech or pharmaceutical industry research and development in drugs to treat osteoarthritis may benefit in biomarkers characterizing cartilage-forming cells. The discovered cell surface protein encoding genes may be beneficial in this quest to develop osteoarthritic drugs. Surgical reconstruction of damaged cartilage with bioengineered cartilage has been evaluated in a clinical trial. The advent of 3D bioprinting/bio-fabrication will enable custom manufacture of engineered cartilage for reconstructive surgery to happen readily. The discovery of the cell surface protein markers discovered here allows for the selection of the most suitable cells for cartilage formation in custom manufacture of bioengineered cartilage. The cell surface protein encoding genes provided herein can be associated with the identification of stem cells that are optimal for cartilage regeneration. Due to the sequence homology, the panel of the genes identified in human to be characteristic of high- or poor-engineered cartilage quality have >80% primary sequence homology with dog and horse. To this end, the gene encoding proteins identified to characterize the cell surface of chondrocytes making either high- or poor-quality cartilage will also have same utility in veterinary regenerative medicine of cartilage.

As further demonstrated in FIGS. 10 to 15, gene expression analysis (quantitative polymerase chain reaction (qPCR) methodology) of ADGRG1 shows that this identified cell surface protein marker as one of several cell surface protein markers discovered in human nasal chondrocytes to correlate with high-quality engineered cartilage are present in horse nasal chondrocytes.

While the description has been described in connection with specific embodiments thereof, it will be understood that it is capable of further modifications and this application is intended to cover any variations, uses, or adaptations including such departures from the present disclosure as come within known or customary practice within the art and as may be applied to the essential features hereinbefore set forth, and as follows in the scope of the appended claims.

What is claimed is:

1. A method of producing a cartilage graft comprising:

expanding autologous chondrocytes from a donor patient;

selecting expanded chondrocytes by detecting the expression of at least one protein gene; and culturing the selected expanded chondrocytes in a culture medium allowing formation of a transplantable cartilage material, wherein the at least one protein gene is ADGRG1, NPR3, SLC16A4, TSPAN13 and/or SLC22A23.

2. The method of claim 1, wherein the chondrocytes are of human or animal origin.

3. The method of claim 2, wherein the chondrocytes are ear chondrocytes, nasal chondrocytes, rib chondrocytes, or knee chondrocytes.

4. The method of claim 2, wherein the chondrocytes are human nasoseptal chondrocytes (hNC) or human sternal chondrocytes.

5. The method of claim 1, wherein the selected chondrocytes are cultured in a 3D culture.

6. The method of claim 1, wherein the selected chondrocytes are co-cultured with mesenchymal stem cells (MSC).

7. The method of claim 6, wherein the MSC are from bone marrow, adipose, synovium, synovial fluid, and from other anatomical sites.

8. The method of claim 7, wherein the MSC are FGF2-expanded human bone marrow mesenchymal stem cells (hBMMSC).

9. The method of claim 1, wherein the culture medium comprises at least one of fibroblast growth factor 2 (FGF-2) and transforming growth factor beta-1 (TGFß1).

10. The method of claim 1, further detecting the expression of at least one protein gene selected from B3GNT7, COLGALT2, IGFBP3, STC2, SAA1, ANGPLT1, COL8A2, INHBB, ADAMTS9, ORM1, COL14A1, DCN, COL21A1, ENOX1, IL7, MXRA5 GAL, TFRC, SERPINA9, LIF, GDF6 and COL5A3.

11. The method of claim 1, wherein the expression of the at least one protein gene is detected by measuring the coded mRNA or encoded protein using a probe.

12. The method of claim 11, wherein the expression of the at least one protein gene is detected by using a nucleic acid probe or an antibody.

13. The method of claim 1, wherein the transplantable cartilage material is a nasal cartilage material.

14. The method of claim 1, wherein the donor patient is a human or an animal.

* * * * *